March 30, 1937. D. LESUEUR Re. 20,315

DIAPER

Original Filed April 30, 1935 2 Sheets-Sheet 1

INVENTOR:
DOROTHY LESUEUR
BY
Frederic R. Wansfield
ATTORNEYS.

March 30, 1937. D. LESUEUR Re. 20,315

DIAPER

Original Filed April 30, 1935 2 Sheets-Sheet 2

INVENTOR.
DOROTHY LESUEUR
BY Frederic P. Vanderbilt
ATTORNEYS.

Reissued Mar. 30, 1937

Re. 20,315

UNITED STATES PATENT OFFICE 20,315

DIAPER

Dorothy Lesueur, Holdenville, Okla., assignor to D. D. D. Manufacturing Company, Ada, Okla.

Original No. 2,049,913, dated August 4, 1936, Serial No. 19,089, April 30, 1935. Application for reissue November 17, 1936, Serial No. 111,226

14 Claims. (Cl. 128—284)

This invention relates to diapers.

The primary object of the invention is to devise a diaper with a permanent washable cloth band with a pocket opening along the lower edge of the band to receive the ends of a disposable pad which admits of quick and easy replacement of the pad after the same has been soiled by the infant.

Another feature of the present invention is to make the band portion of the diaper in two separate sections which sections are designed to be relatively narrow above the hips of the infant which construction enables the maximum freedom of movement of the legs.

Another object of the invention is to provide a diaper formed of a woven textile fabric band and a disposable absorbent pad that permits the circulation of air to the body of the person or infant wearing the diaper which is a wide departure from diapers using rubber or rubberized fabrics in such construction because the rubber or rubberized fabrics inhibit the circulation of air to the body.

Further objects of the invention are the provision of a diaper having the separate disposable part constructed so that it promotes efficient sterilization prior to using it thereby fostering highly sanitary methods of caring for infants, invalids and involuntary bed-ridden patients in hospitals to prevent diseases incident to laundered diapers such as skin irritations and diaper rash; and that admits of being used not only on infants but for adult involuntary bed-ridden patients in hospitals and for permanent invalids; and that is strong, compact and durable, that is highly efficient in operation, and that may be manufactured at very low cost.

With the foregoing and other objects in view the invention consists of a novel construction, combination and arrangement of parts as will be hereinafter more specifically described and illustrated in the accompanying drawings wherein is disclosed an embodiment of the invention but it is to be understood that changes, variations and modifications may be resorted to without departing from the spirit of the claims hereunto appended.

In the drawings wherein like reference characters denote corresponding parts throughout the several views.

Figure 1:
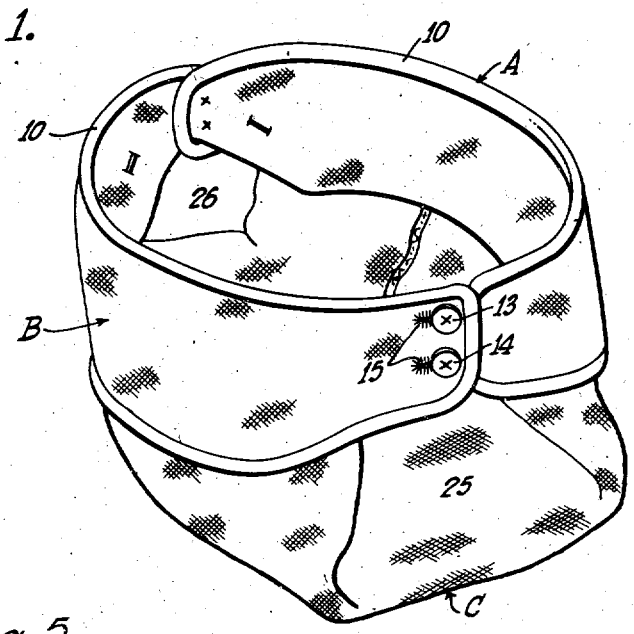
Figure 1 is a perspective view of the diaper of the present invention in assembled relation as it would appear when secured upon an infant.
Figure 5:
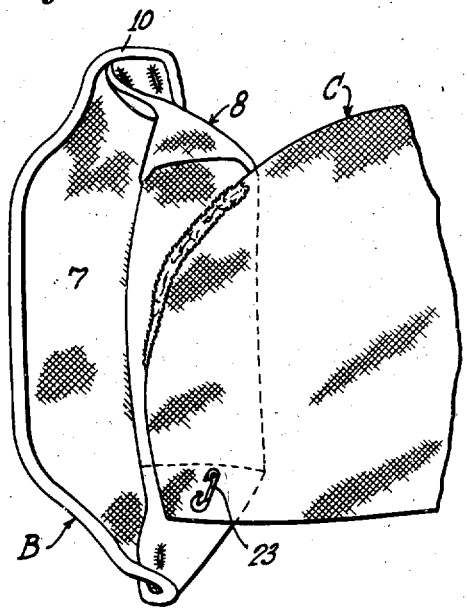
Figure 5 is a perspective view of a portion of the pad and one section of the band showing the pocket opened and the manner of attaching an end of the pad to the inner layer of the section.

Referring to the drawings in detail the diaper is constructed of a band having a back section indicated generally at A detachably connected to the front section B between which sections of the band is a pendant pad C. The pad C is easily detached from the sections of the band to allow replacement thereof when the pad is soiled by the infant. As will appear in Figure 1 of the drawings the pendant pad C conforms to the crotch of the infant.

Figure 2:
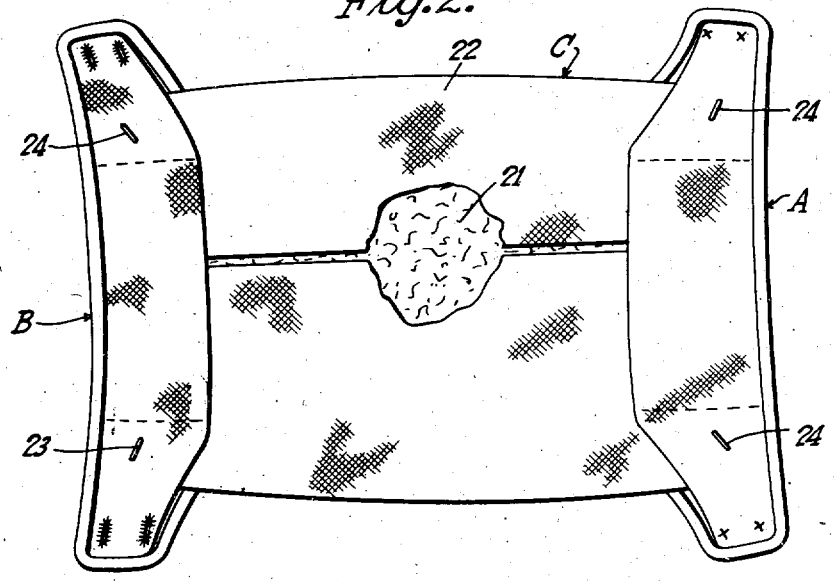
Figure 2 is an inside plan view of the diaper in open position and partly broken away.
Figure 3:
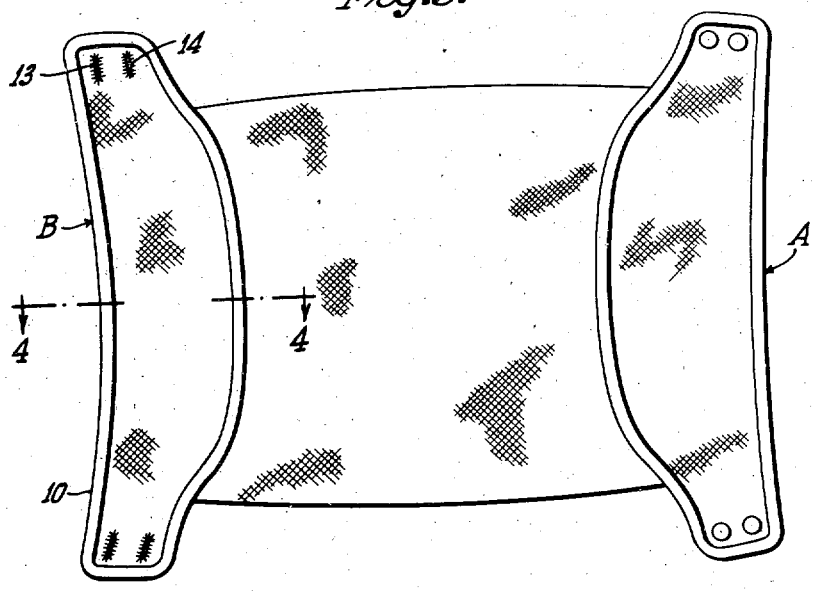
Figure 3 is an outside plan view of the diaper in open position.
Figure 4:
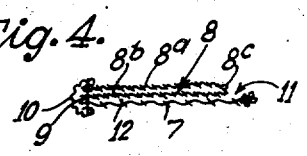
Figure 4 is a sectional view taken substantially on the plane of line 4—4 of Figure 3 and looking in the direction of the arrows.

The height in the center of the back section A of the band is greater than the height of the front section B. The upper edge of back section A is straight while the upper edge of the front section B is curved which features will appear from an inspection of Figures 2 and 3 of the drawings.

With the exception of the differences pointed out above sections A and B of the band are both formed alike and a description of the one will teach the construction of the other. Each section consists of an elongated body made of washable, closely woven cloth fabric and is constructed of a front layer 7 and a rear layer 8 both of which conform to each other with respect to shape but the front layer 7 is slightly longer than the rear layer 8 which will appear from an inspection of Figures 2 and 3. Rear layer 8 is doubled to form the parts 8a and 8b with the fold 8c along the lower edge. The upper free edges of the parts 8a and 8b as well as the side margins thereof are secured to the edges of front layer 7 by stitching 9 which anchors the binding 10 to these edges.

The lower edges of the inner layer 8 and the outer layer 7 are separated to provide an entrance 11 to the pocket 12 between these layers. It will be understood that with the exception of the lower edges all the remaining portions of the outer layer 7 and the inner layer 8 are secured together by the stitching 9 and binding 10. From an intermediate portion, looking at Figs. 2 and 3, the sections A and B decline outwardly along the lower edges to the ends of the sections to provide relatively narrow parts of the band in the neighborhood of the hips to admit freedom of the legs.

Figure 6:
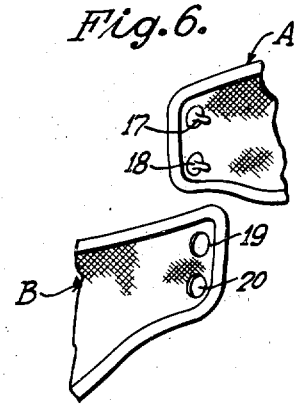
Figure 6 is an exploded view of the confronting ends of the sections of the band illustrating a modified form of the fastening devices to hold the sections together.

To secure the back section A in detachable relation to the front section B each end of the back section A is provided with spaced buttons 13, 14 which register with buttonholes 15, 16 on the ends of the front section B. In the modified form (illustrated in Fig. 6) of detachably securing the ends of back section A to the ends of front section B there are a pair of spaced male separable fasteners 17, 18 which coact with the female separable fasteners 19, 20 on the ends of front section B.

The pad C is substantially rectangular in shape. The pad C has an inner panel 21 of suitable thickness which is highly absorbent and the panel is limp enough to comfortably conform to the shape of the crotch of the infant. The panel 21 is preferably formed of matter such as cellulose fibre of suitable softness. Folded about the panel 21 is a sheet of gauze 22 which forms an envelope for the panel and this gauze conforms in shape to the panel. Inasmuch as the fibrous panel 21 offers a certain amount of cohesion, it is not necessary to stitch the gauze to the panel.

The opposite ends of the pad C extend through the entrances 11 along the bottom edge of the sections and into the pockets 12 of each section. The ends of pad C are detachably secured to the inner layers 8 by means of the safety pins 23, 24.

The length of the pad C will vary in infants of different sizes so as to make the pendant portion of the pad comfortable. When the pad C is secured to the sections of the band the pendant portion will assume a relatively flat fold having openings 25, 26 at each side through which the legs of the infant extend.

There is a decided advantage in the feature of the present invention which allows the soiled disposable pad to be replaced by a fresh pad without exposing the body of the infant or person to any great extent.

With the person or infant reclining on their backs the front end of the disposable pad C is unpinned from the layer 8 of front section B, and the end of the replacing fresh pad is pinned to the layer 8. At this point the rear end of pad C is unpinned with the body still resting in a supine position. With the replacing pad attached to the front section of the band, and the soiled pad separated therefrom, the person or infant is raised. While raised, the soiled pad is doubled to cover the soiled area and then slipped outwardly free of the body. At the same time the fresh replacing pad is trained about the crotch and up the back next to the body of the infant or person. When the replacing pad is in this position the ends lie in proximity to the back section of the band and the person or infant that has been raised may be lowered on the fresh replacing pad. By turning the person or infant from side to side the back end of the pad may be inserted in the pocket between the layers of the back section of the band and pinned to the inner layer 8 of the back section A. It will thus be seen that one raising of the body is sufficient to remove the soiled and apply the fresh disposable pad, and the time of exposure of the body is reduced to a minimum.

Having thus described the invention, what is claimed as new is:

1. A diaper and in combination, a waist band formed with a front and back section, each section made in two layers of washable fabric substantially conforming in shape with each other, the layers of the sections being separated along their lower edges and joined together about the remaining portions of their areas to provide a downwardly opening pocket between the two layers, a substantially rectangular disposable panel suspended between the sections to supply a pendant area to conform to the crotch of the infant, said pad including a bibulous pad enveloped by a gauze cover, the ends of said panel extending into the pocket on each section and detachably secured to one layer of each section, and the ends of each section carrying coacting means for detachably securing the sections together.

2. A diaper and in combination, a waist band formed with a front and back section, each section made in two layers of washable fabric substantially conforming in shape with each other, the layers of the sections separated along their lower edges and joined together about the ends and upper edges thereof to provide a downwardly opening relatively long pocket between the two layers, a substantially rectangular disposable panel suspended between the sections to supply a pendant area to conform to the crotch of the infant, said pad including a bibulous pad enveloped by a gauze cover, the ends of said panel extending into the pocket on each section and detachably secured at spaced-apart points to one layer of each section, the ends of each section carrying coacting means for detachably securing the sections together, and the centers of the sections being wider than the ends to provide a relatively narrow part of the band over the hips to allow freedom of movement of the legs.

3. A diaper, comprising in combination, a waist band comprising a front and a back section, each said section having a convex downwardly curved lower edge, said front section comprising an elongated inner body of washable fabric folded along its lower edge and back upon itself to form a double layer having its longitudinal edges adjacent each other and having its lower edge curved convexly and comprising an outer layer of relatively strong washable fabric, said outer fabric layer and said inner double layer having their adjacent upper and end edges stitched together; thereby forming a downwardly opening separable pocket; spaced apart fastener elements on the free end of said back section; cooperative interlocking fastener elements on the free end of said front section for releasably engaging said fastener elements on said back section; a relatively flat panel of fabric material, an inner absorbent pad contained within said fabric panel, the opposite ends of said panel and inclosed pad being insertable respectively into the pockets of said front and back waist band sections and adapted to be releasably attached therein.

4. A diaper comprising, in combination, a waist band comprising a front and a back section, said front section comprising an elongated inner body of washable fabric forming a double layer having its longitudinal edges adjacent each other and having its lower edge curved convexly and downwardly, and comprising an outer layer of relatively strong washable fabric having convexly curved lower edge and of an area substantially equal to the area of said inner double fabric body, said outer fabric layer and said inner double layer having their adjacent upper and end edges stitched together; a binding strip about said upper and end edges of each said front and back sections respectively, said binding strip and said adjacent edges of said inner fabric body and said outer layer being stitched together; spaced apart fastener elements on the free end of said back section; cooperative interlocking fastener elements on the free end of said front section for releasably engaging said fastener elements on said back section; a relatively flat panel of fabric material, an inner absorbent pad contained within said rectangular fabric panel, the opposite ends of said panel and inclosed pad being insertable respectively into the pockets of said front and back waist band sections and adapted to be releasably attached therein.

5. A diaper comprising, in combination, a waist band comprising a front section and a separable back section; cooperative fastener elements on said back and front sections respectively; said front section consisting of an outer relatively strong washable fabric panel and an inner double fabric body the upper and end edges of said outer fabric panel and said double panel body being stitched together to form a downwardly opening separable pocket; said back waist band section comprising an outer fabric panel and an inner double fabric body formed of fabric and folded to present its longitudinal edges adjacent each other and upon the longitudinal upper edge of said back waist band section; stitching along the opposite ends and upper edge of said outer fabric panel and said double fabric body to secure the same together, and an absorbent fibrous pad having the opposite ends thereof inserted in said pockets respectively and releasably attached therein.

6. A diaper and in combination a waist band formed with a front and a back section, each section made in two layers of washable fabric substantially conforming in shape with each other, the layers of the sections being separated along their lower edges and joined together about the remaining portions of their areas to provide a downwardly opening pocket between the two layers, a substantially rectangular disposable panel suspended between the sections to supply a pendant area to conform to the crotch of the infant, the said panel including a bibulous pad enveloped by a gauze cover, the ends of the said panel extending into the pocket on each section and detachably secured to one layer of each section, and the ends of each section carrying means for securing the sections together.

7. A diaper and in combination a waist band formed with a front and a back section, each section made in two layers of washable fabric substantially conforming in shape with each other, the layers of the sections being separated along their lower edges and joined together about the ends and upper edges thereof to provide a downwardly opening relatively long pocket between the two layers, a substantially rectangular disposable panel suspended between the sections to supply a pendant area to conform to the crotch of the infant, the said panel including a bibulous pad enveloped by a gauze cover, the ends of the said panel extending into the pocket on each section and detachably secured at spaced apart points to one layer of each section, and means for securing the sections together, the centers of the sections being wider than the ends to provide a relatively narrow part of the band over the hips to allow freedom of movement of the legs.

8. A diaper and in combination a waist band formed with a front and back section, each section made in two layers of washable fabric substantially conforming in shape with each other, the layers of the sections separated along their lower edges and joined together about the ends and upper edges thereof to provide a downwardly opening relatively long pocket between the two layers, a substantially rectangular disposable panel suspended between the sections to supply a pendant area to conform to the crotch of the infant, the said panel including a bibulous pad enveloped by a gauze cover, the ends of the said panel extending into the pocket on each section and detachably secured at spaced apart points to one layer of each section, the ends of each section carrying means for securing the sections together, and the centers of the sections being wider than the ends to provide a relatively narrow part of the band over the hips to allow freedom of movement of the legs.

9. A diaper comprising, in combination, a waist band comprising a front and a back section, each of the said sections having a convex downwardly curved lower edge, and comprising an elongated inner layer of washable fabric and an outer layer of relatively strong washable fabric, the said outer fabric layer and the said inner layer having their adjacent upper and end edges stitched together, thereby forming a downwardly opening separable pocket, spaced apart fastener elements on the free end of the back section, cooperative interlocking fastener elements on the free end of the front section for releasably engaging the said fastener elements on the said back section, a relatively flat panel of fabric material, an inner absorbent pad contained within the said fabric panel, the opposite ends of the said panel and inclosed pad being insertable respectively into the pockets of the said front and back waist band sections and adapted to be releasably attached therein.

10. A diaper comprising, in combination, a waist band comprising a front and a back section, each section comprising an elongated inner body of washable fabric having its lower edge curved convexly and downwardly and comprising also an outer layer of relatively strong washable fabric having convexly curved lower edge and of an area substantially equal to the area of the inner fabric body, the outer fabric layer and the inner layer having their adjacent upper and end edges stitched together, a binding strip about the said upper and end edges of each of the said front and back sections respectively, the said binding strip and the adjacent edges of the inner fabric layer and the outer layer being stitched together, spaced apart fastener elements on the free end of the back section cooperative interlocking fastener elements on the free end of the front section for releasably engaging the fastener elements on the back section, a relatively flat panel of fabric material, and an inner absorbent pad contained within the said rectangular fabric panel, the opposite ends of the said panel and inclosed pad being insertable respectively into the pockets of the said front and back waist band sections and adapted to be releasably attached therein.

11. A diaper comprising, in combination, a waist band comprising a front section and a back section, cooperative fastener elements on the back and front sections respectively, the said front section consisting of an outer relatively strong washable fabric panel and an inner fabric body, the upper and end edges of the outer fabric panel and the inner fabric body being stitched together to form a downwardly opening separate pocket, the said back waist band section comprising an outer fabric panel and an inner fabric body, stitching along the opposite ends and upper edge of the said outer fabric panel and the said inner fabric body to secure the same together, thereby forming a downwardly opening separable pocket, and an absorbent fibrous pad having the opposite ends thereof inserted in the said pockets respectively and releasably attached therein.

12. A diaper comprising, in combination, a waist band comprising a front section and a back section, means for fastening the sections together, the said sections comprising outer and inner relatively strong washable fabric panels having upper and end edges stitched together to form downwardly opening pockets, and an absorbent fibrous pad having the opposite ends thereof inserted in the pockets respectively and releasably attached therein.

13. A diaper and, in combination, a waist band formed with a front section and a back section, each section comprising layers of washable fabric substantially conforming in shape with each other and defining a downwardly opening pocket for each section extending substantially the length of each section, a disposable, substantially rectangular pad assembly having its ends inserted in the pockets so that the said pad assembly is suspended between the sections to supply a pendant area to conform to the crotch of the infant, the said pad assembly comprising a panel-shaped inner pad of highly bibulous, limp material and a limp moisture-permeable envelope therefor conforming to the shape of the inner pad, means detachably securing the ends of the pad assembly to one of the layers of the pockets of the waist band sections, and means at the ends of each of the waist band sections for securing the said sections together.

14. A diaper and, in combination, a waist band formed with a front section and a back section, each section comprising layers of washable fabric defining a downwardly opening pocket for each section of the waist band extending substantially the length of each of the said sections, a disposable panel-like pad assembly having its ends inserted in the said pockets, the said pad assembly comprising a panel-shaped inner pad of highly absorbent, limp material conforming to the crotch of a wearer and a sheet of gauze folded about the inner pad to conform to the shape thereof, the ends of the said panel extending into the pocket on each section and detachably secured to one layer of each section, and the ends of each section carrying means for securing the sections together.

DOROTHY LESUEUR.